United States Patent
Lowe et al.

(10) Patent No.: US 10,039,617 B2
(45) Date of Patent: Aug. 7, 2018

(54) VIBRATING ORTHODONTIC STRIP

(71) Applicant: ORTHOACCEL TECHNOLOGIES INC., Bellaire, TX (US)

(72) Inventors: Michael K. Lowe, Houston, TX (US); Lawrence W. Swol, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 267 days.

(21) Appl. No.: 14/422,252

(22) PCT Filed: Sep. 16, 2013

(86) PCT No.: PCT/US2013/059928
§ 371 (c)(1),
(2) Date: Feb. 18, 2015

(87) PCT Pub. No.: WO2014/047004
PCT Pub. Date: Mar. 27, 2014

(65) Prior Publication Data
US 2015/0182305 A1      Jul. 2, 2015

Related U.S. Application Data

(60) Provisional application No. 61/704,724, filed on Sep. 24, 2012.

(51) Int. Cl.
*A61C 3/00* (2006.01)
*A61C 7/00* (2006.01)
*A61C 7/08* (2006.01)

(52) U.S. Cl.
CPC ............... *A61C 7/008* (2013.01); *A61C 7/08* (2013.01)

(58) Field of Classification Search
CPC .......... A61C 7/008; A61C 7/08; A61C 19/063
(Continued)

(56) References Cited

U.S. PATENT DOCUMENTS

| 7,223,270 B2* | 5/2007 | Altshuler | ........... A46B 15/0002 433/29 |
| 2008/0227046 A1* | 9/2008 | Lowe | ...................... A61C 7/00 433/2 |

(Continued)

FOREIGN PATENT DOCUMENTS

| WO | WO2010093632 | 8/2010 |
| WO | WO2013155366 | 10/2013 |

OTHER PUBLICATIONS

Worlds Smallest Coin Vibration Motor at 8mm Diameter is Ideal for Handheld Alerting, Published on Mar. 13, 2011 at 24/7PressRelease, http://www.24-7pressrelease.com/press-release/worlds-smallest-coin-vibration-motor-at-8mm-diameter-is-ideal-for-handheld-alerting-201577.php.*

(Continued)

*Primary Examiner* — Cris L Rodriguez
*Assistant Examiner* — Mirayda A Aponte
(74) *Attorney, Agent, or Firm* — Boulware & Valoir

(57) ABSTRACT

A low cost disposable peel-and-stick vibrating orthodontic strip can be attached to existing orthodontic devices such as aligners, thus speeding dental remodeling by as much as 50%. A low cost orthodontic appliance generally in the form of a peel-and-stick vibrating strip that can be advantageously applied to existing orthodontic devices, such as aligners, positioners, fixed appliances, or even applied directly to teeth.

19 Claims, 13 Drawing Sheets

(58) Field of Classification Search
USPC .......... 433/6, 18, 24, 171; 128/861; 601/30
See application file for complete search history.

(56) References Cited

U.S. PATENT DOCUMENTS

| | | |
|---|---|---|
| 2008/0227047 A1 | 9/2008 | Lowe |
| 2009/0061379 A1* | 3/2009 | Yamamoto .............. A61C 7/00 433/24 |
| 2010/0055634 A1* | 3/2010 | Spaulding ............... A61C 7/00 433/5 |
| 2011/0136070 A1* | 6/2011 | Rubin ................... A61C 7/008 433/2 |
| 2011/0184265 A1* | 7/2011 | Hayter .................... A61B 5/01 600/347 |
| 2012/0040300 A1 | 2/2012 | Levens |
| 2012/0322018 A1 | 12/2012 | Lowe |
| 2013/0059263 A1 | 3/2013 | Lowe |
| 2013/0252193 A1 | 9/2013 | Bowman |
| 2014/0023983 A1 | 1/2014 | Lowe |

OTHER PUBLICATIONS

Coin Vibration Motors by Precision Microdrives—https://www.precisionmicrodrives.com/vibration-motors/coin-vibration-motors.*

Chung How KAu, et al., The clinical evaluation of a novel cyclical force generating device [AcceleDent(R)] in orthodontics, Orthodontic Practic 1(1): 10-15 (2010).

Kopher RA and Mao JJ. Suture growth modulated by the oscillatory component of micromechanical strain. 2003. J. Bone and Min. Res. 18(3). pp. 521-528.

Nishimura et al. Periodontal tissue activation by vibration: Intermittent stimulation by resonance vibration accelerates experimental tooth movement in rats. 2008. Am J Orthod Dentofacial Orthop 133(4) pp. 572-283.

Peptan al, et al. Responses of intramembranous bone and sutures upon in-vivo cyclic tensile and compressive loading. 2008. Bone (42) pp. 432-438.

Vij K. and Mao, JJ. Geometry and cell density of rat craniofacial sutures during early postnatal deveopment and upon in-vivo cyclic loading. 2006. Bone (38) pp. 722-730.

Krishtab et al., Use of vibratory action on the teeth to accelerate orthodontic treatment. Stomatologiia (Mosk). May-Jun. 1986; 65(3):61-3.

* cited by examiner

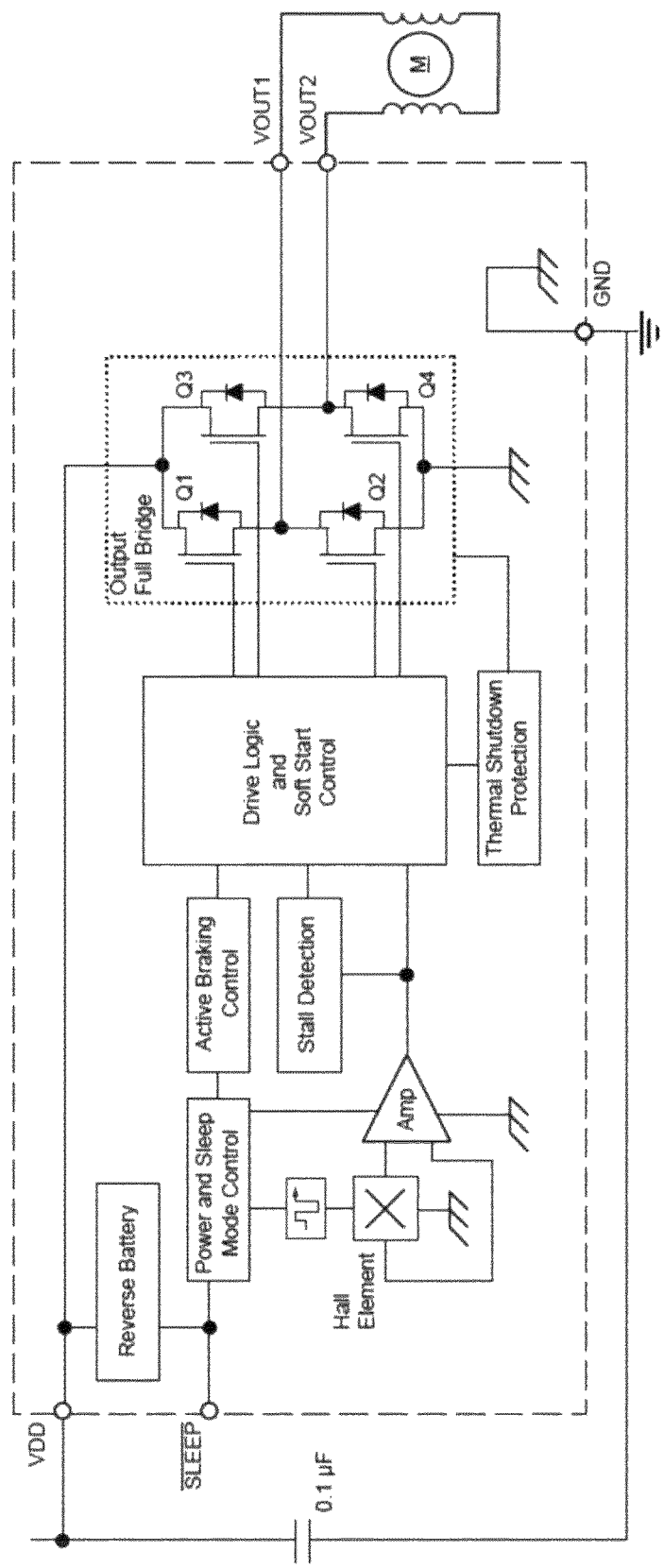
Figure 5. A1442 BLDC vibration motor driver functional block diagram.

VIBRATING ORTHODONTIC STRIP

This application is a National Phase under 35 U.S.C. § 371 of International Application PCT/US2013/59928, filed Sept. 16, 2013, which claims priority to 61/704,724, filed Sept. 24, 2012. Each of these is incorporated by reference in their entirety for all purposes.

FEDERALLY SPONSORED RESEARCH STATEMENT

Not applicable.

FIELD OF THE INVENTION

This invention relates to vibrating devices for use in orthodontic remodeling.

BACKGROUND OF THE INVENTION

A malocclusion is a misalignment of teeth or incorrect relation between the teeth of the two dental arches. The term was coined by Edward Angle, the "father of modern orthodontics," as a derivative of occlusion, which refers to the way opposing teeth meet. Angle based his classifications of malocclusions on the relative position of the maxillary first molar. According to Angle, the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variations therefrom result in malocclusion.

There are three classes of malocclusions—Class I, II, and III. Further, class II is subdivided into three subtypes:

Class I: Neutrocclusion In Class I the molar relationship of the occlusion is normal or as described for the maxillary first molar, but the other teeth have problems like spacing, crowding, over or under eruption, etc.

Class II: Distocclusion (retrognathism, overjet) In this situation, the upper molars are placed not in the mesiobuccal groove, but anteriorly to it. Usually the mesiobuccal cusp rests in between the first mandibular molars and second premolars. There are two subtypes:

Class II Division 1: The molar relationships are like that of Class II and the anterior teeth are protruded.

Class II Division 2: The molar relationships are class II but the central incisors are retroclined and the lateral incisors are seen overlapping the central incisors.

Class III: Mesiocclusion (prognathism, negative overjet) In class III malocclusions the upper molars are placed not in the mesiobuccal groove, but posteriorly to it. The mesiobuccal cusp of the maxillary first molar lies posteriorly to the mesiobuccal groove of the mandibular first molar. This malocclusion is usually seen when the lower front teeth are more prominent than the upper front teeth. In such cases, the patient very often has either a large mandible or a short maxillary bone.

Orthodontics, formerly orthodontia (from Greek orthos "straight or proper or perfect"; and odous "tooth"), is the first specialty of dentistry that is concerned with the study and treatment of malocclusion (improper or dysfunctional bite), which may be a result of tooth irregularity, disproportionate facial skeleton relationship, or both. Orthodontics treats malocclusion through the displacement of teeth via bony remodeling and control and modification of facial growth.

This process has been traditionally accomplished by using static mechanical forces to induce bone remodeling, thereby enabling teeth to move. This widely accepted approach to treating malocclusion takes about twenty-four months on average to complete, and the time cannot be shortened by increasing the force, due to the pain and risk of root resorption with excess force. In this approach, orthodontic braces consist of an archwire that applies a continuous static force to the dentition and interfaces with brackets that are affixed to each tooth. Such braces are used to treat a number of different classifications of clinical malocclusion. These clinical malocclusions include underbites, overbites, cross bites, open bites, and crooked teeth, for both aesthetic and functional/structural reasons.

Orthodontic treatment is complicated by the fact that it is uncomfortable and/or painful for patients, and the orthodontic appliances are perceived as unaesthetic, all of which creates resistance to use. Further, the 24-month treatment time is very long, and further reduces usage and compliance, which can include chronic poor dental hygiene. In fact, some estimates provide that less than half of the patients who could benefit from such treatment elect to pursue orthodontics.

Kesling introduced the tooth-positioning appliance in 1945 as a method of refining the final stage of orthodontic finishing after debanding. A positioner was a one-piece pliable rubber appliance fabricated on the idealized wax set-ups for patients whose basic treatment was complete. Kesling also predicted that certain major tooth movements could also be accomplished with a series of positioners fabricated from sequential tooth movements on the set-up as the treatment progressed. However, this idea did not become practical until the advent of 3D scanning and computer modeling in 1997.

Removable clear appliances, such as the Invisalign® system, have been introduced for treating malocclusion, and provide greatly improved aesthetics since the devices are transparent. However, because these appliances can be removed, compliance can be an issue, and failure to use at least 22 hours a day slows the overall treatment time.

As a treatment modality, aligners are also limited in the classifications of clinical malocclusion that they can address. In the past, aligners have not been able to easily rotate or extrude teeth because the aligner cannot adequately direct force in all directions. Conditions that can be difficult to treat with an Invisalign® appliance or are contra-indicated altogether include:

crowding and spacing over 5 mm
skeletal anterior-posterior discrepancies of more than 2 mm (as measured by discrepancies in cuspid relationships)
centric-relation and centric-occlusion discrepancies
severely rotated teeth (more than 20 degrees)
open bites (anterior and posterior) that need to be closed
extrusion of teeth
severely tipped teeth (more than 45 degrees)
teeth with short clinical crowns
arches with multiple missing teeth.

Being aware of these limitations, Align Technologies has recently combined the Invisalign® clear aligners with clear attachments that adhere to teeth and can provide a surface on which force can be exerted in any desired direction. A custom mold is made using a 3D model of the patients teeth with pockets therein for the placement of a force attachment, the placement and shape of which are determined using proprietary modeling software. The relevant force attachments are made and fitted into the mold, adhesive applied to the attachments, and the mold applied to the teeth. This allows precise and quick placement of the clear attachments, which are then affixed using light cure. There is some affect on aesthetics, but because the force attachments are also clear, they are not very noticeable from a distance.

In addition to static forces, cyclic or pulsed forces (e.g., vibration) can also be used for orthodontic remodeling. Kopher and Mao assessed cyclic forces of 5 Newtons peak magnitude at 1 Hz in rabbits, while Peptan and Mao assessed cyclic forces of 1 N at 8 Hz in rabbits, and Vij and Mao assessed cyclic forces of 300 mN at 4 Hz in rats. In aggregate, the data from these three studies indicated that cyclic forces between 1 Hz and 8 Hz, with forces ranging from 0.3 N to 5 N, increased bone remodeling. Rates depended on different methodologies, but increases of 2.5× with vibrational forces were common. Since Dr. Mao's experiments, an independent study out of Japan has confirmed and strengthened the idea of vibration at 60 Hz for speeding orthodontic tooth movement, and an earlier 50 Hz study in Russia also confirms the basic premise. In fact, by now there is a well-established literature confirming the efficacy of this treatment modality.

The early Mao studies provided a basis for both possible efficacy and likely safety for using vibration in humans to assist orthodontic tooth movement. However, the original force (5 Newton) and devices were completely unsuitable for human use, and it was unclear that rabbit cranial results would be applicable to human dentition. Thus, considerable additional effort was needed to translate the promising results into a human suitable, commercially successful device.

OrthoAccel® Technologies Inc., invented and clinically tested the first commercially successful orthodontic vibrating device, as described in US2008227046, designed to apply cyclic forces to the dentition for accelerated remodeling purposes. Both intra-oral and extra-oral embodiments are described in US2008227046, each having processors to capture and transmit patient usage information. The bite plate was specially designed to contact occlusal as well as lingual and/or facial surfaces of the dentition, and thus was more effective than any prior art devices in conveying vibrational forces to the teeth.

Further, the device has actually been tested in a double blind clinical trial and has been shown to speed orthodontic remodeling as much as 50%. As such it is truly a breakthrough in orthodontic technology (Kau 2010, see also clinicaltrials.gov). Finally, the device is slim, capable of hands free operation, lacks the bulky headgear of the prior art devices, and has optimized force and frequency for orthodontic remodeling. Thus, its comfort level and compliance was also found to be high, with patients reporting that they liked the device, especially after the motor was redesigned to be quieter and smoother, as described in US2010055634 et seq. In fact, this device has been marketed as AcceleDent® in Australia, the United Kingdom, Europe, China, South Korea, Japan, Kenya, and the United States and has achieved remarkable commercial success since its recent introduction (2009). AcceleDent® represents the first successful clinical approach to accelerate orthodontic tooth movement by modulating bone biology in a non-invasive and non-pharmacological manner.

However, further improvements in the above device are always beneficial, and this application addresses some of those improvements.

SUMMARY OF THE INVENTION

In one aspect, the invention is a low cost orthodontic appliance generally in the form of a peel-and-stick vibrating strip that can be advantageously applied to existing orthodontic devices, such as aligners, positioners, fixed appliances, or even applied directly to teeth.

The peel-and-stick embodiment may be preferred as having the lowest profile and simplicity of manufacturing, but many other attachment means are possible, including magnetic attachment, snap fit attachments, hook attachments, separate spring clasp attachments and the like.

One preferred shape is a rectangular strip size to be applied to lingual (or buccal) surfaces of teeth. The entire dentition can be covered with a strip of 10-15 cm or two or three strips can be used instead. Another possible shape is the traditional U-shaped plate similar to the existing bite plates. Combinations are also possible. However, the simple elongated rectangular strip design is expected to provide the lowest cost device and simplicity of manufacture.

The flexible strip is waterproof, and contains one or more small vibratory sources (aka vibrators), power sources, optional on/off switch and has the relevant connections needed to operably connect the components such that vibration can be applied to the device and thus to the teeth.

On/off switches may be optional, and instead, the device can be preprogrammed to vibrate once or twice or more times per day for a suitable period of time, such as about 10-20 minutes. In such embodiment, it may be determined to be equally efficacious to trade frequency for duration, thus vibrating the teeth more often during the day, but for shorter time periods.

In preferred embodiments, the device is fairly simple and thus can be manufactured for lower cost, such that a patient could by a package of e.g., 24 strips that can be used with a series of, e.g., clear aligners or positioners. In such embodiments, compliance monitoring and programmability features can be omitted. In other embodiments, such features could be included, but probably at a higher price point.

A processor can control, sample, and compensate for the speed/force of the vibratory source. The processor can run software that captures usage frequency and duration and can be programmed to change the force, frequency, waveform, amplitude, duration or any other operating parameter. The processor can communicate usage frequency and duration to a remote computer via any type of wired or wireless communication method. The processor can communicate with the remote computer over the Internet, via smartphone, etc.

Preferably, a custom or semi-custom application-specific integrated circuit (ASIC) is designed to drive the device. An ASIC can include entire microprocessors, memory blocks including ROM, RAM, EEPROM, Flash and other large building blocks. Such an ASIC is often termed a SoC (system-on-chip). Hardware description language (HDL), such as Verilog or VHDL, can be used to describe the functionality of ASICs. Field-programmable gate arrays (FPGA) are another option for driving the device. Programmable logic blocks and programmable interconnects allow the same FPGA to be used in many different applications. For smaller designs and/or lower production volumes, FPGAs may be more cost effective than an ASIC design even in production.

Another viable option is to use structured ASIC design (also referred to as "platform ASIC design"), because both manufacturing cycle time and design cycle time are reduced compared to cell-based ASIC, by virtue of there being pre-defined metal layers (thus reducing manufacturing time) and pre-characterization of what is on the silicon (thus reducing design cycle time). Design differentiation and customization is achieved by creating custom metal layers that create custom connections between predefined lower-layer logic elements. "Structured ASIC" technology is seen as bridging the gap between field-programmable gate arrays and "standard-cell" ASIC designs. Because only a small number of chip layers must be custom-produced, "structured ASIC" designs have much smaller non-recurring expenditures than "standard-cell" or "full-custom" chips, which require that a full mask set be produced for every design.

The smallest, cost effective vibrators of suitable speed and force characteristics are preferred for use as the vibratory source. A large number of very small vibrating motors are commercially available, as shown in the table below, but piezoelectric motors may be preferred due to the small size, and off-set weighted motors may be preferred due to low cost and availability. Particularly preferred are the substantially planar motors where the vibration is substantially parallel to the substrate (e.g., U.S. Pat. Nos. 5,554,971, 5,780,958, US2009224616, US2008129130, US2007103016, WO0178217, each incorporated by reference). Vibrations may be oscillating, random, directional, circular, and the like. Vibrators are well within the skill of the art, and several are described in the patent literature. For example, US2007299372, US2007255188, US2007208284, US2007179414, US2007161931, US2007161461, US2006287620, each incorporated by reference, describes various vibrating motors.

Hundreds of vibrating motors (aka vibratory sources) are commercially available, a few of which are as follows:

Integrated optical encoders may be preferred, as one type of rotary encoder, but the feedback mechanism can be any known technology. Encoders can be separate or integrated, and be optical, magnetic, or capacitive encoders. A proportional-integral-derivative controller (PID controller) is another option. The PID is a generic control loop feedback mechanism widely used in industrial control systems.

A DC 6V Motor having off-set weight and 8 line integrated encoder is known to provide the required characteristics, but many other vibrators can also provide these performance characteristics, and can be easily tested for same. MicroMo Inc., for example has 8 and 16 line encoders integrated with micromotors available at a variety of voltages, and many other suppliers make similar devices. As another option, Allegro has a low profile motor driver A1442 that is quiet, reliable and can be combined with most brushless motors. Its very small size makes it ideal for an application such as this, and the driver is described in more detail below and shown in FIG. 5, although fully integrated packages may be preferred.

It is possible however, that since this device is entirely intra-oral that there will be minimal variability of speed, since the patient dos not bite on the strip, nor handle an extra-oral component. Thus, feedback features can probably be omitted.

A non-rechargeable or wirelessly rechargeable battery are preferred power sources for driving the vibratory source, but

| Company | Catalog | Size | Specifications |
|---|---|---|---|
| ELLIPTEC AG ™ | NA See U.S. Pat. No. 6,870,304 | 10 × 3 × 2 mm | 3-6 volts piezoelectric motor |
| SURPLUS TRADERS ™ | MF918 | 0.45 × 0.16 inches | 1 VDC to 5 VDC 18 ohms Weighted shaft |
| MOTOROLA ™ | G13566 | 0.44 × 0.18 inches | 1 VDC to 9 VDC 10 ohms Weighted shaft |
| PRECISION MICRODRIVE | 308-100 | 8 × 3.4 mm | 3 v DC shaftless coin vibration motor, 12,000 RPM (200 Hz), 0.7 g (6.87 m/s$^2$) |
| PRECISION MICRODRIVE | 304-103 | 4.4 × 3.5 mm | 3 V DC surface mount reflow solderable coin vibration motor. 14000 RPM (233 Hz) at 2.7 V, 0.5 G (4.91 m/s$^2$) of vibration amplitude. The motor vibration efficiency is typically 2.8 G/W, but a typical current draw of 65 mA keeps the current low enough for battery powered applications. |
| Kotl | C1020B008F1 | 10 mm × 2 mm | 3 V DC motor |

Preferably, the vibrating component has a more stable vibrator with improved performance characteristics of decreased sound and low variance frequency and force. In particular, the improved vibrator has a noise level less than 55 dB when measured at 6 inches, a frequency at 20-40 Hz, with a variance of only 2 Hz, and a force of 0.1-0.5 Newtons, with a variance of +−0.05 N, or similar.

Consistency of frequency and force can be achieved via a feedback loop whereby motor speed is monitored and software adjusts the motor as needed. More particularly, the motor contains an integrated encoder that provides multiple high and low signal outputs per motor revolution. The software counts the time between every encoder event (e.g., a rotating disc with markings thereon can be optically sensed) and compares this to the desired target (e.g., 30 Hz). Based on this comparison, the software then adjusts the pulse width modulation that is driving the motor to increase or decrease speed as appropriate to maintain the desired speed. Accurate controlling of speed also controls the force.

charged capacitors can also be used since the devices need have only a limited power life. Small coin batteries, alkaline or lithium, are preferred due to their small size, but hydrogen batteries may also be preferred due to their power and power density, particularly as size and cost decrease with further technological development.

For certain embodiments, a battery that can be wirelessly recharged is preferred for longer product life (e.g., US2009051312, U.S. Pat. No. 7,511,454), but in other embodiments a low cost device is manufactured that is intended to be single patient use and need only last a week or two. It is known in the art to select an appropriate power source/motor combination to provide an orthodontic vibrator that vibrates within the frequency and power suitable for orthodontic remodeling.

Any off the shelf on/off switch can be used, although the switch is optional if the device is preprogrammed to runs 2 or more times per day. Particularly preferred for an intraoral device is an on/off switch with depressible activator (push button, rocker or membrane button). The on/off switch can be located on any convenient surface, or an additional surface can be provided just for the switch, e.g., a small ledge provided on the molars for easy activation.

The orthodontic remodeling device preferably has a very steady quiet motor. Particularly preferred is a noise level less than 55 dB when measured at 6 inches, and a vibration frequency of 10-50, preferably 20-40 Hz, or 30 Hz, with a variance of only 2 Hz, and a force of 0.0.5-0.5 Newtons, preferably 0.1-0.3 N, or 0.2-0.25 N, with a variance of +−0.05 N, or similar.

Methods of orthodontic remodeling, are also provided, comprising applying the strip to an existing orthodontic remodeling device, as described above, and activating the vibrator for about 5, 10, 15 or 20 minutes or more. This can be daily, or preferably twice daily, or more.

By vibrating "strip" herein what is meant is that a long, thin, rectangle is provided that is shaped to fit lingual (or buccal) surfaces of the teeth. Thus, the strip would be 3-15 cm in length, and 5-10 mm in height, and easily fit against lingual or buccal surface of an aligner. By vibrating "plate" in contrast, what is meant is a U-shaped plate that fits the occlusal surfaces of the teeth and thus is shaped to fit the common arch forms. Combinations thereof, are of course possible, but for simplicity and cost reduction a simple strip is preferred. Regardless of shape, the thickness of the device should be minimized to reduce bulk and discomfort.

By "daily" usage herein, what is meant is at least 67% daily compliance. Perfect compliance would be preferred, but 50% faster orthodontic remodeling (e.g., one year v. two) has been clinically demonstrated at the force and frequency herein described.

By "50% faster" orthodontic remodeling or similar such phrase, what is meant is that the time need to complete a case can be reduced by half, provided of course that the orthodontist proceeds more quickly with the treatment plan. Thus, aligners need to be changed every week, instead of every two weeks to achieve this reduction in treatment time.

By "connector" what is meant herein is the male end of a male-to-female connector, wherein the "socket" is the female end into which the connector or plug fits. Attachment means do not necessarily include a socket, however, and any two compatible shapes can be used.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term consisting essentially of excludes such elements as bulky head gear, tooth brush bristles, lasers, and the like, which would fundamentally change the nature and use of the device. The phrase would not, however, exclude elements such as additional control features, battery charge indicators, variations in wiring, or variations in software, processor or communication technology, and the like.

BRIEF DESCRIPTION OF THE DRAWINGS

FIG. 3 shows shorter peel-and-stick vibrating strip, designed to be used with any existing devices, especially aligners and positioners, and the like.

FIG. 4 shows a long peel-and-stick vibrating strip, designed to be used with any existing devices, especially aligners and positioners, and the like.

FIG. 5. Circuit diagram for exemplary motor driver, the Allegro A1442.

FIG. 6 shows various snap fit attachment means.

FIG. 7 shows various hook attachment means. FIG. 7A is a hook and eye attachment means, while

FIG. 8 shows various separate attachment means.

FIG. 9A shows a ball and socket snap fit in a vertical orientation, FIG. 9B shows an over the retainer hook or spring clasp, FIG. 9C shows an under the retainer hook, FIG. 9D shows a bracket into which the strip can fit, and FIG. 9E shows a pair of compatible attachment means, in this case hooks, in a horizontal orientation.

DETAILED DESCRIPTION OF THE INVENTION

Generally speaking, the vibrating orthodontic remodeling device is provided as an inexpensive peel-and-stick device, designed to be used with other devices, such as aligners. Although the peel-and-stick embodiment may be preferred, any attachment means can be used, including spring clasps, which can be used with any aligner. Alternatively, the aligner can be modified to include one half of an attachment means, such as a metal insert for magnetic coupling, or a snap fit connector or socket for same, and the like.

Figure 1:
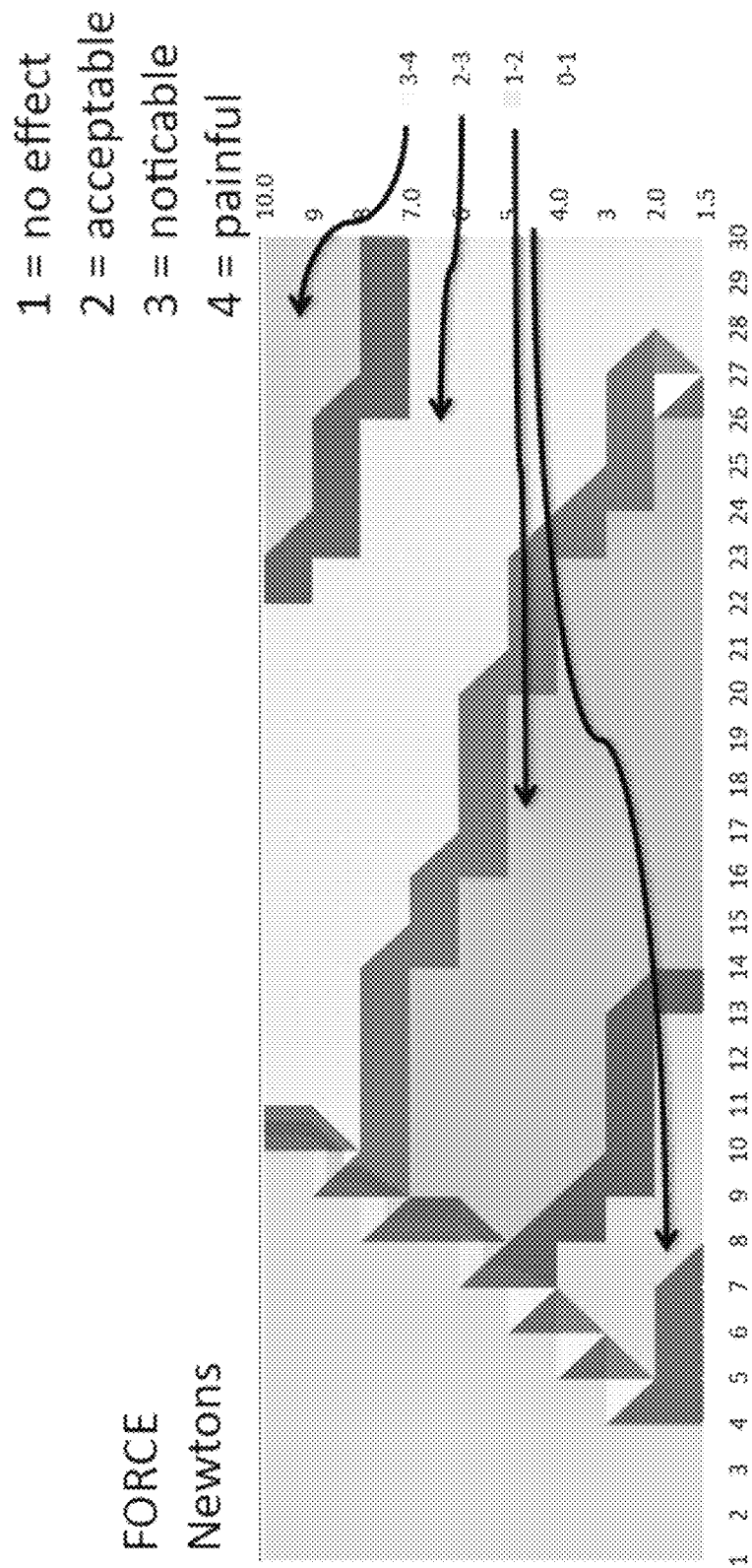
FIG. 1 shows a graph of force in Newtons on the Y axis, versus frequency in Hz on the X axis, and plotted are patient reactions to the various combinations of force and frequency. Generally, the higher the frequency, the less force should be used in order to provide a device that will have good patent acceptance.

FIG. 1 shows what force and frequency combinations have been shown to be acceptable for good patient compliance. Generally speaking, the higher the frequency, the less force should be used. Thus, frequencies of less than 1 N and less than 100 HZ are preferred. Particularly preferred are frequencies of 10-50 HZ, 5-20 Hz, or 20-40 HZ, and 0.05-0.5 Newtons, 0.1-0.3N, 0.2-0.25 N, are preferred. The existing AcceleDent® Aura device is 30 Hz and 0.25 N, and the original Phase III device was 30 Hz and 0.2 N.

Figure 2:
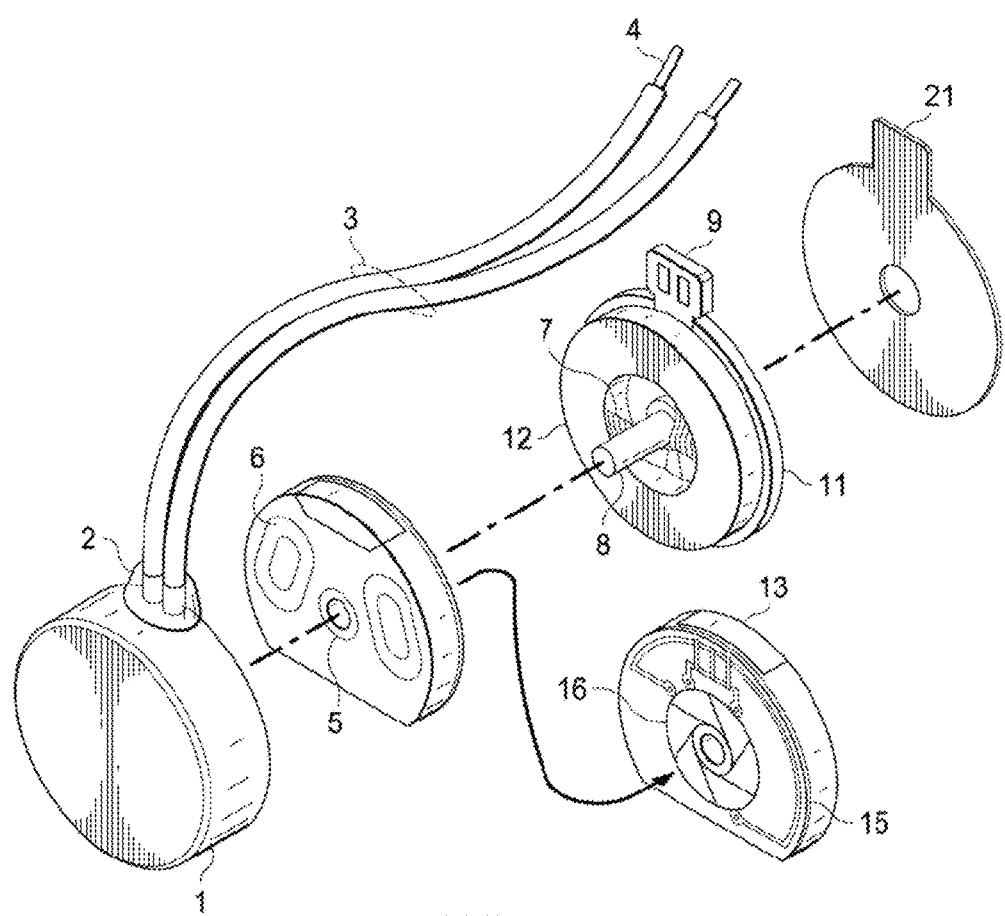
FIG. 2 shows an exemplary coin or pancake motor, known in the art and commercially available.

Many tiny vibrators are commercially available, as noted above, and one exemplary such device available e.g., from Precision MicroDrives, is shown in FIG. 2. FIG. 2 is a typical coin or pancake vibrating motor enclosed inside a motor case 1 with flying leads 3 emerging therefrom, protected at the case end by a drop of UV epoxy or other adhesive 2, and having bare wires 4 shown at the opposite end. The case 1 is backed, in this case with an adhesive mounting back 21. Inside the case 1 is motor chassis 11 having a magnet 12 (e.g., a NdFeB neodymium magnet), brushes 7, and motor shaft 8, which fits through bearing 5. Commutator 16 and commutation circuitry 15, together with voice coil windings 6 and H-bridge circuitry for active braking (not shown) control the device, but many other control means are possible. When the motor is driven the shaft 8 rotates, turning the eccentric counterweight 13, causing vibration. Flex PBC 9 allows electric connections.

Brushed coin vibration motors are constructed from a flat PCB on which the 3-pole commutation circuit is laid out around a central shaft. The vibration motor rotor consists of two 'voice coils' and a small mass that are integrated into a flat plastic disc with a bearing in the middle, which sits on a shaft. Two brushes on the underside of the plastic disc make contact to the PCB commutation pads, to provide power to the voice coils, which generate a magnetic field. This field interacts with the flux generated by a disc magnet that is attached to the motor chassis. The commutation circuit alternates the direction of the field through the voice coils, and this interacts with the N-S pole pairs that are built into the neodymium magnet. Consequently, the disc rotates, and due to the built in off-centered eccentric mass, the motor vibrates.

However, the above is only one type of commercially available vibration motor, and many different motor designs are available, including Linear Resonant Actuator (LRA) vibration motors, also known as linear vibrators, brushless vibration motors, miniaturized DC coreless vibrating motors, and the like.

The smallest motors that can be accurately controlled are generally preferred, thus, fully integrated motor and driver packages of height less than 4 mm, preferably less than 3 mm, are preferred. Further, since the devices of the invention can be manufactured with multiple motors, the force generated by an individual motor can be quite low.

It is also known in the art how to provide quiet reliable motors with minimal variance in force and speed and 6 and 8 line encoders are one method of controlling the motor. As another example, the Allegro A1442 is a full-bridge motor driver designed to drive low-voltage, brushless DC motors. Commutation of the motor is achieved by use of a single Hall element sensor to detect the rotational position of an alternating-pole ring magnet. A high-density CMOS semiconductor process allows the integration of all the necessary electronics. This includes the Hall element sensor, the motor control circuitry, and the full output bridge. Low-voltage design techniques have been employed to achieve full device functionality down to low VDD values. This single chip driver solution provides enhanced reliability (including reverse battery protection and output short circuit protection) and eliminates the need for any external support components. The A1442 also employs a soft-switching algorithm to reduce audible switching noise and EMI interference. A micropower sleep mode can be enabled by an external signal, to reduce current consumption for battery management in portable electronic devices. This feature allows the removal of a FET transistor for switching the device on and off. See FIG. 5, which shows the circuit diagram for this driver. The A1442 is optimized for vibration motor applications in cellular phones, pagers, and the like, and the low profile make this device ideally suited for use in applications where printed circuit board area and component headroom are at a premium. Further, it is available in a lead (Pb) free, 6 pin MLP/DFN microleadframe package, with an exposed pad for enhanced thermal dissipation.

In addition to the many commercially available off-the-shelf fully integrated vibration motor and driver packages, a custom or semi-custom motor package can be designed and manufactured. Due to the precise requirements needed for orthodontic remodeling, as well as the significant size constraints, it is expected that a custom motor will be needed, and that compliance monitoring and/or feedback control may be eliminated to conserve space.

Figure 3:
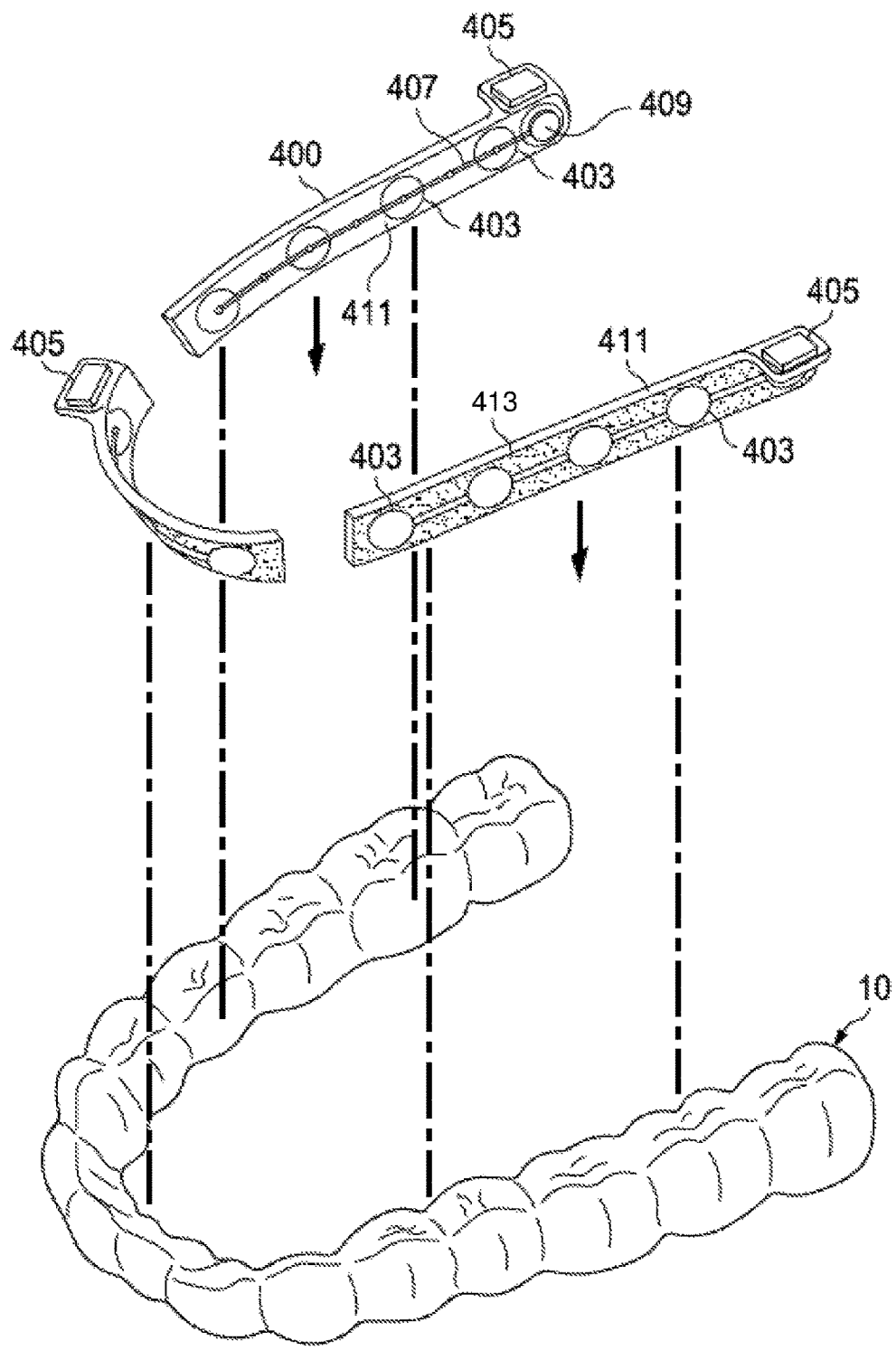
Figure 4:
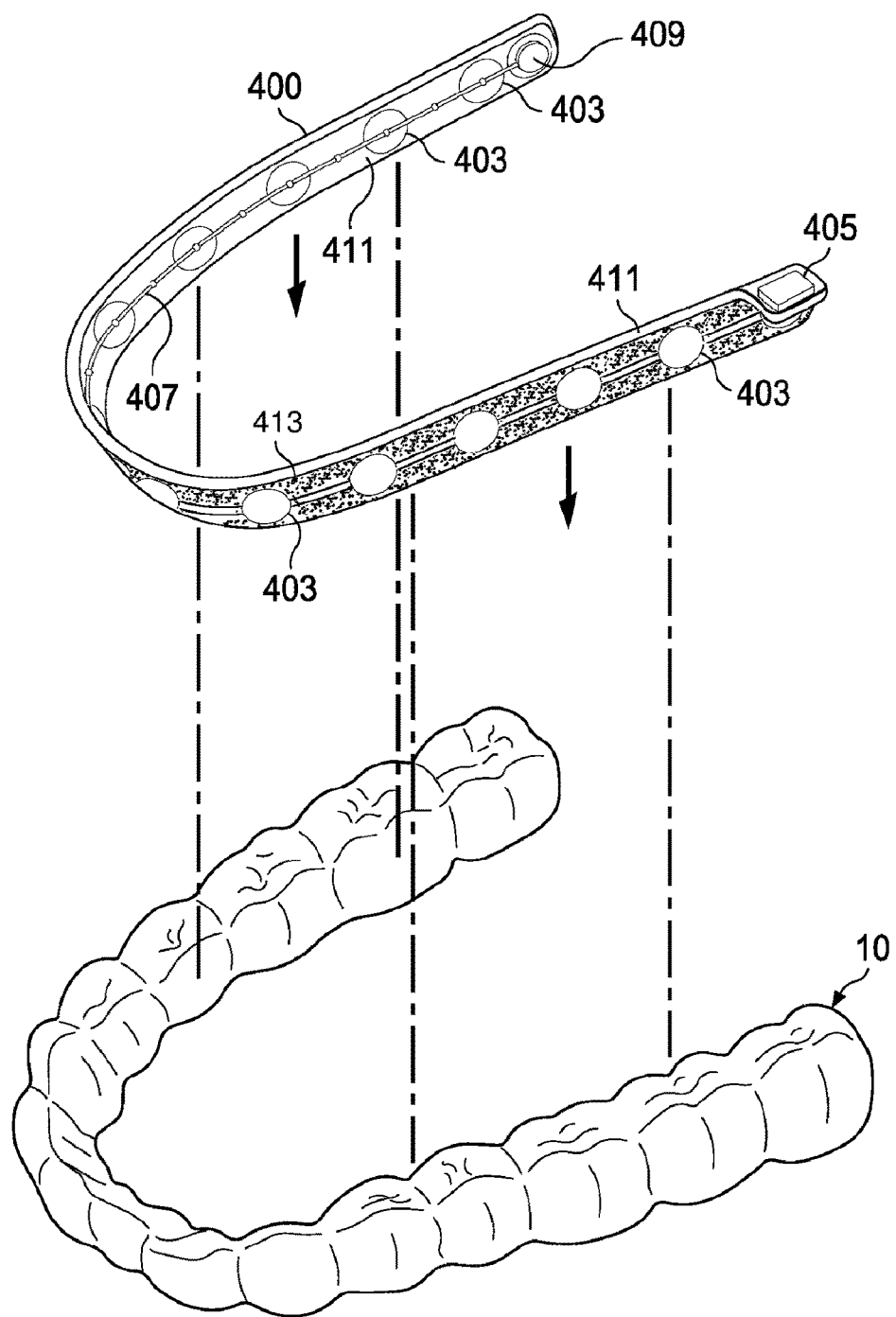

FIGS. 3 and 4 show peel and stick vibrating strips that can be applied to existing aligners and positioners, and the like, thus speeding their remodeling effect. The device can be provided as shorter strips, as in FIG. 3, such that two or three are required for use on each of the upper and lower arches (assuming that both arches require orthodontic remodeling). Alternatively, the strip can be a single longer strip as in FIG. 4, designed to contact the entirety of the upper or lower dental device.

The embodiment in FIG. 3 are shorter, flexible strips that can be combined and used buccally on the sides, and optionally also lingually in front, or they can all be used lingually on the aligner 10. An on/off switch 405 is connected via wires 407 to one or more batteries 409. The on/off switch 405 can be positioned anywhere convenient, here shown in a position that can be contacted with a molar, but it can also be on the flat side of the strip and actuated with a finger. The optional on/off switch 405 connects to one or more vibratory sources 403, which upon actuation will vibrate the strip. The device 400 is hermetically sealed inside a plastic coating or housing 411.

The embodiment in FIG. 4 is a longer strip, which usually will be used on the lingual surface of the aligner 10 so as to be invisible. A simple, flexible strip having an on/off switch 405 connected via wires 407 to one or more batteries 409. The on/off switch 405 also connects to one or more vibratory sources 403, which upon actuation will vibrate the strip, and thus, to device to which the strip is attached.

Preferably the vibratory source 403 is a piezoelectric motor or coin vibrator, but other devices may serve the same function. Several coin vibrators are shown along the length of the device in FIG. 4, but fewer can be used. This particular embodiment can also have two or more coin batteries or charged capacitors located along the strip, as needed to power the multiple vibrators.

Coating or housing 411 seals the entire device. Preferable, the coating or housing is flexible enough to allow the strip to be bent to used with various sized aligners, e.g., 30-70 Shore A and has a smooth lingual surface with low profile, and a flat back surface, with adhesive layer (413) and protective layer (not shown, but well known in the art).

The strip can be made sufficiently rigid such that the vibration from the vibratory source 403 can be transmitted to the entire strip, which in turn transmits to the existing aligners, positioners, bite plates and the like. Alternatively, the use of several vibrators 403 can serve the same purpose and allow for a more flexible housing material.

It is also noted that the vibratory source 403 does not necessarily locate at one end or a particular location along the strip, but can be variably positioned so long as it is electrically and mechanically feasible to do so with the least hindrance to the user.

Housing materials should be of a biocompatible, tasteless material or coated with same. Plastics are generally preferred, especially medical grade silicone rubbers. The housing can be molded from two surfaces, attached together along the sides with the electronic components inside, or applied via a curable liquid coating. In one manufacturing method, the components are applied to a thin base layer which supports the components in the required position and orientation, and the entire device dip coated or spray coated to be completely sealed and thus waterproof.

The device can be combined with more sophisticated electronics, such as a ASIC chip to control and record usage data, as well as electronics for wireless transmission, but in a peel-and-stick strip such components can be omitted for a low cost disposable device that does not allow usage monitoring or post-manufacturing variation of parameters.

Preferably, a water resistant and biocompatible adhesive is used since the device will be used inside the mouth. Several such adhesives are known in the denture and medical device industries. Such adhesives are taught e.g., in US2012028219, EP 1324732.

In a variation on this theme, it is possible that the strip can be attached magnetically (depending on the materials the aligner or positioner is made of), rather than with adhesive, and thus be removed when not in use. For example, a small magnetically active element can be placed within the material of the aligner, e.g., on the lingual surfaces where they will not be visible, allowing the strips to be mounted magnetically.

Other attachments means are also possible, but low or no profile attachment means are preferred since there is limited room inside the mouth. For example, the aligner can be fabricated with a protruding ball that fits into a small socket on the strip (or vice versa), so that the parts connect in the same way that small circular snaps are used to attach clothing items. See for example FIGS. 6 and 7, which illustrate embodiments of a vibrating strip or plate for which some aligner modification is necessary. Note, the vibrational components are omitted from these figures for clarity, but are well known and are as described above or in the incorporated references.

Figure 6A:
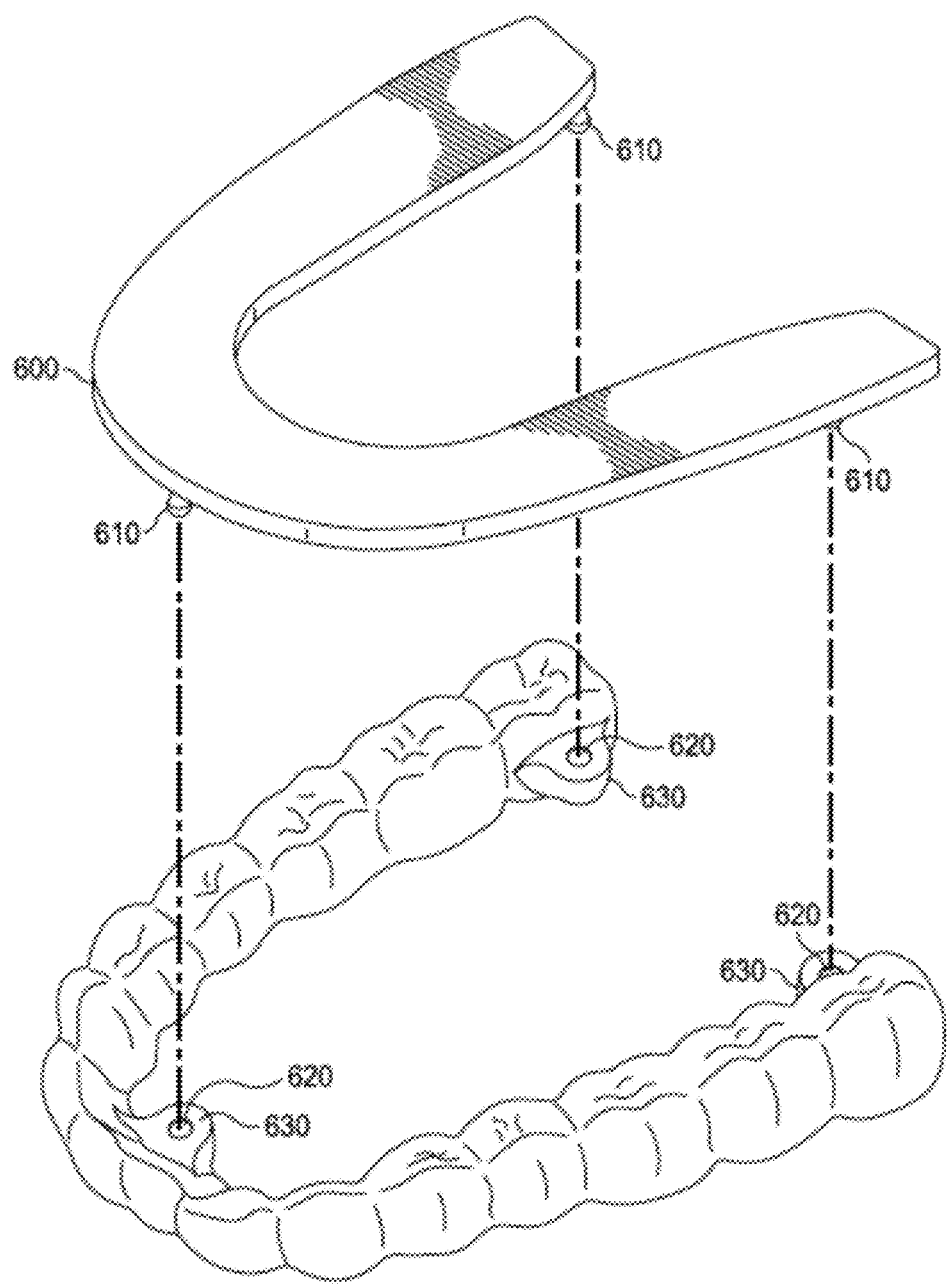
FIG. 6A is an aligner and strip snap fitted into place with a ball and socket snap. Either component could be fitted with the female end, and the other with the male end.

FIG. 6A shows a vibrating orthopedic plate that contacts occlusal surfaces, as opposed to lingual surfaces as shown in the embodiments of FIGS. 3 and 4. In FIG. 6A a flat bite 600 plate connects to an aligner that has been provided with a protrusion 630 on the lingual surface, in this case three protrusions, one central and two posteriorly positions. A socket 620 is provided in the protrusion 630, into which a correspondingly shaped connector 610 on the bite plate fits. In this case, the connector and socket are a ball and socket snap fit, and the size is exaggerated for clarity. In actuality, the protrusion and connector can be quite small. Although the bite plate shown allows occlusal contact, a lingual vibrating strip could be made using the same principles. Additionally, the male and female ends can be reversed.

Figure 6B:
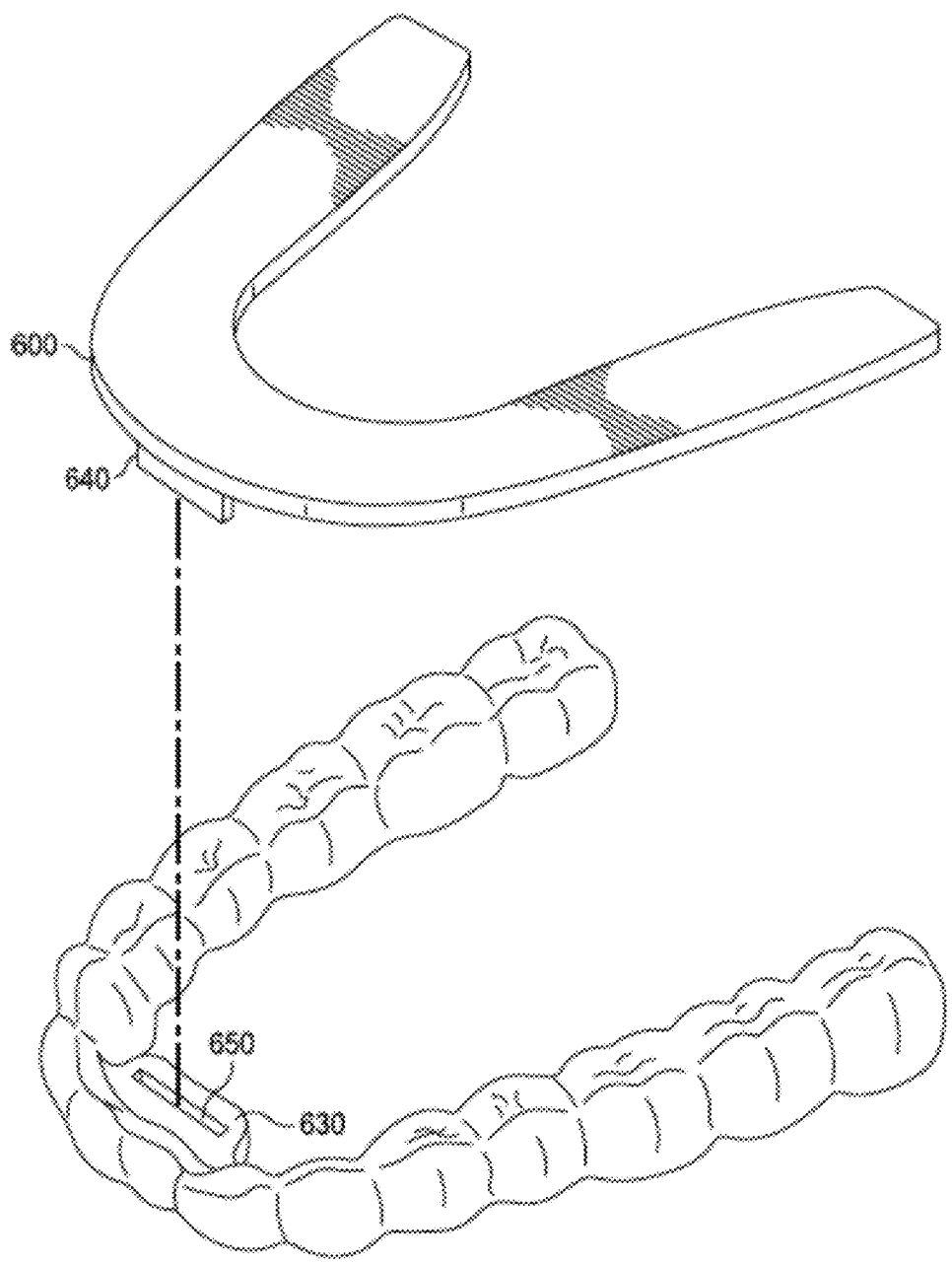
FIG. 6B shows a central port, rectangular in shape similar to a USB port or phone connector, wherein the strip has a corresponding thin rectangular projection to fit thereinto.

FIG. 6B shows a variation on 6A wherein only a single central protrusion 630 occurs, in this case outfitted with a rectangular socket 650 into which a rectangular connector 640 fits. This can be a simple friction fit, or prongs can be provided for a snap fit (not shown). Alternatively, a pair of connectors can fit over the front and back of an aligner (not shown), and no aligner modification would thus be needed.

Figure 7A:
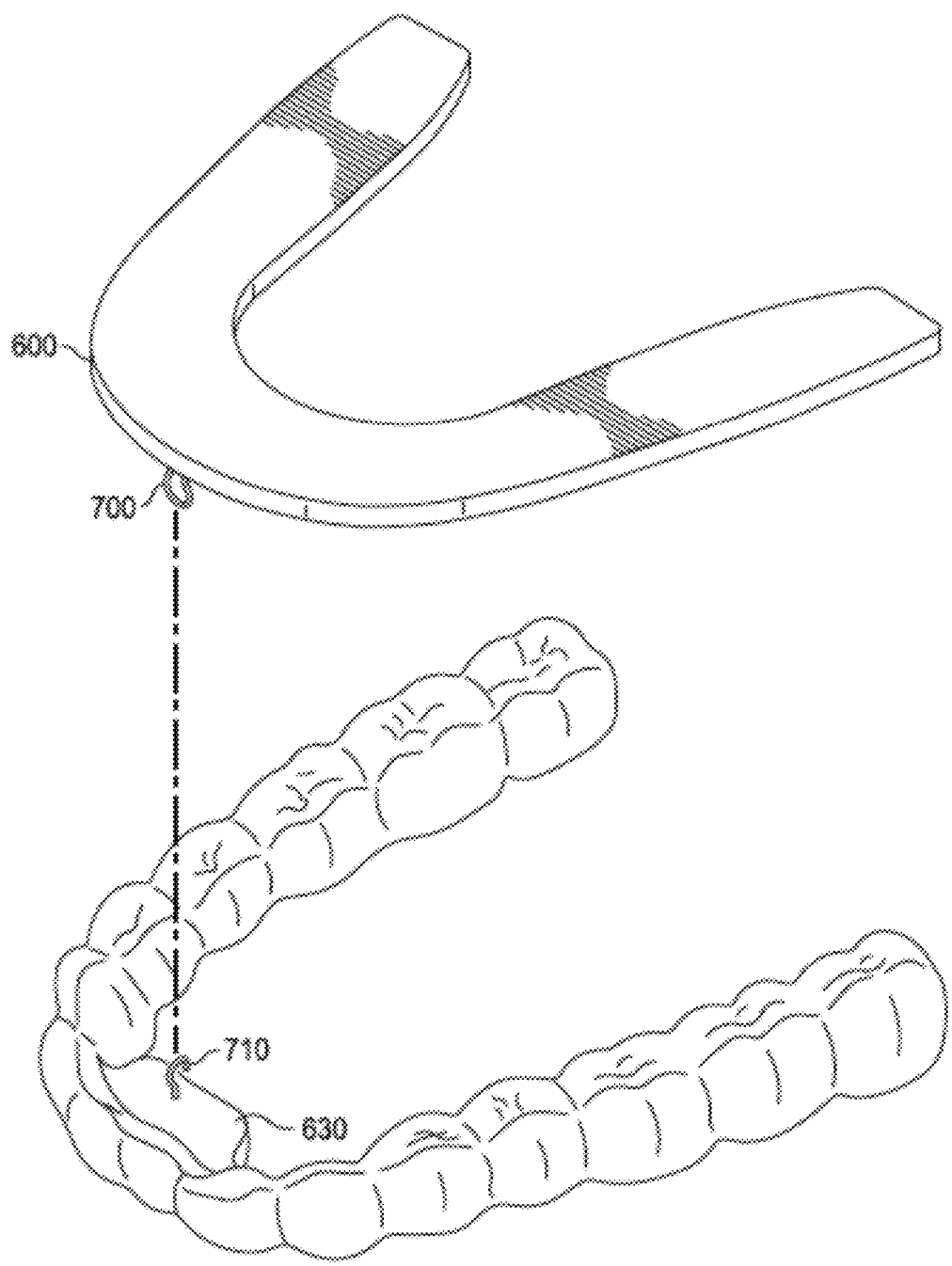
Figure 7B:
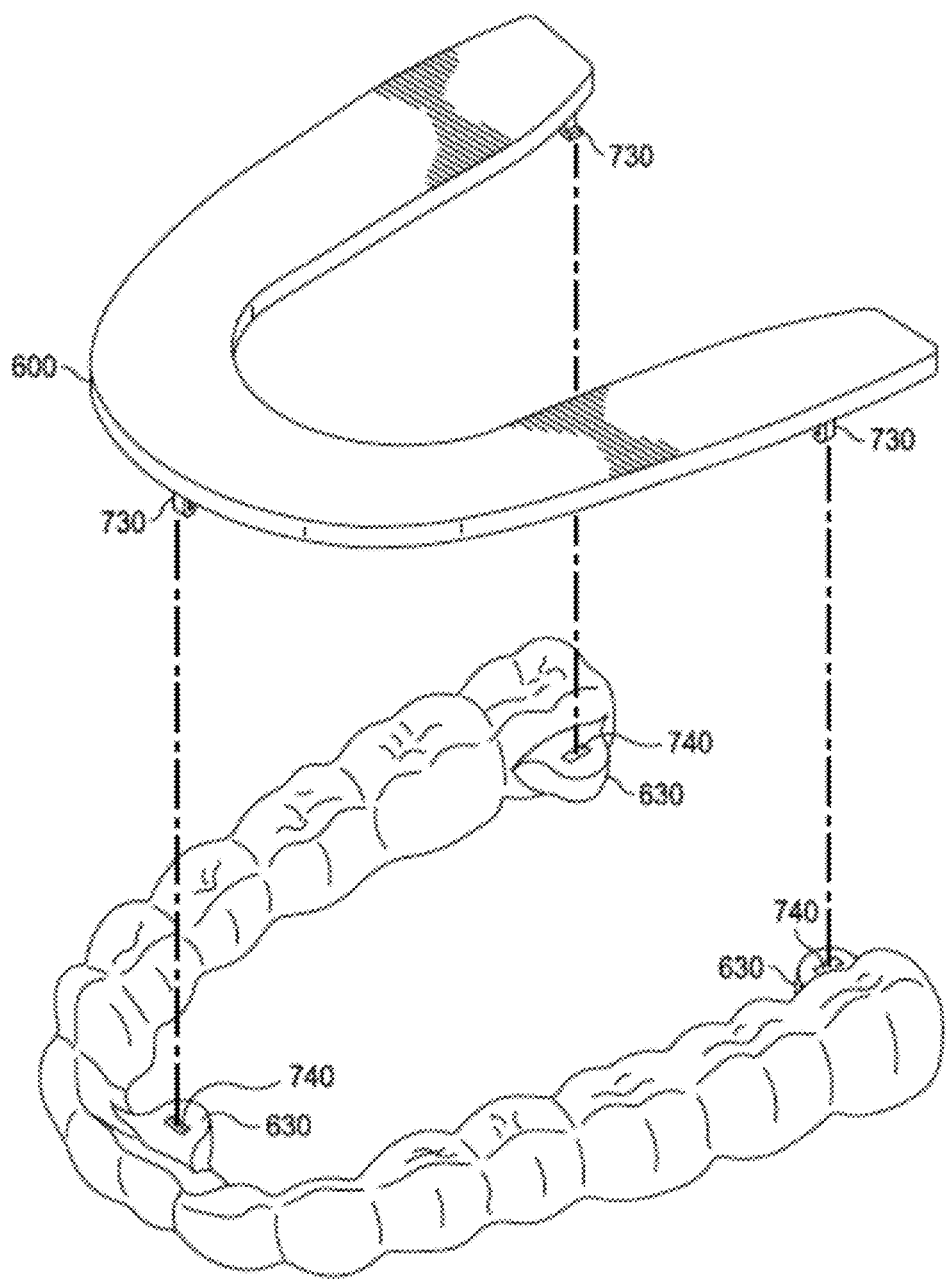
FIG. 7B shows a hook fitting into a slot socket on the aligner.
Figure 7C:
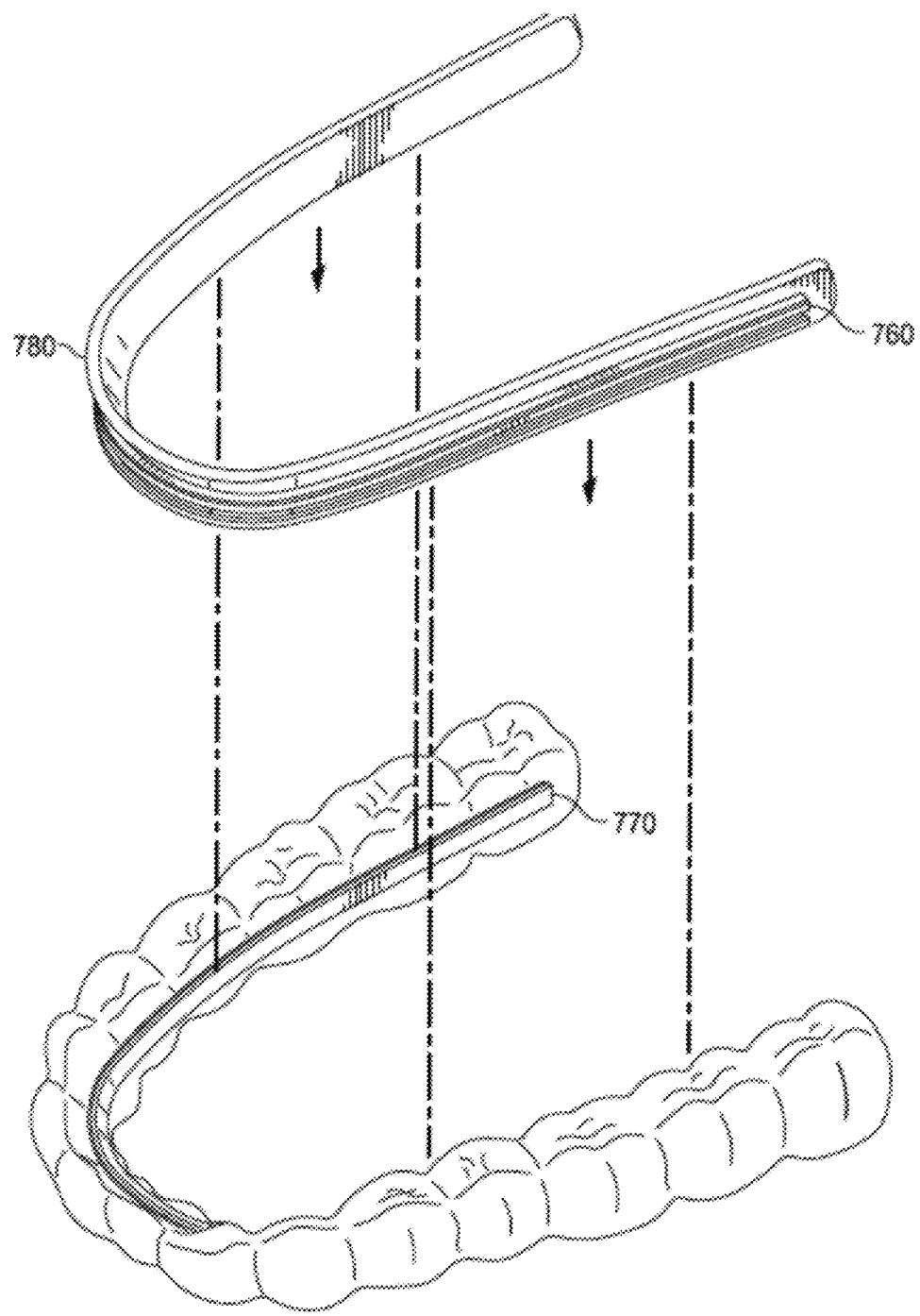
FIG. 7C shows a strip 780 with hooked upper and lower edges 760 along the length of strip 780, where the rims can be grippingly hooked over a small protruding rim 770 provided on the aligner.

FIG. 7A-C shows additional variations on the theme of making an aligner with a dedicated attachment point 630 provided for a mating attachment means on the plate and/or strip. FIG. 7A shows a simple eye 700 and hook 710. FIG. 7B shows a snap fit wherein a snap fit connector 730 fits into a socket shaped to accept same. FIG. 7C shows a single connector 760 mating with another connector 770. In this instance connector 760 is a pair of hooked edges (e.g. forming a C-shaped clamp in cross section) running the length of the strip 780, which hook over the small protruding rim or edges 770 (e.g., forming a sideways T in cross section) provided on the aligner, but any gripping or mating shapes could be used.

Figure 8A:
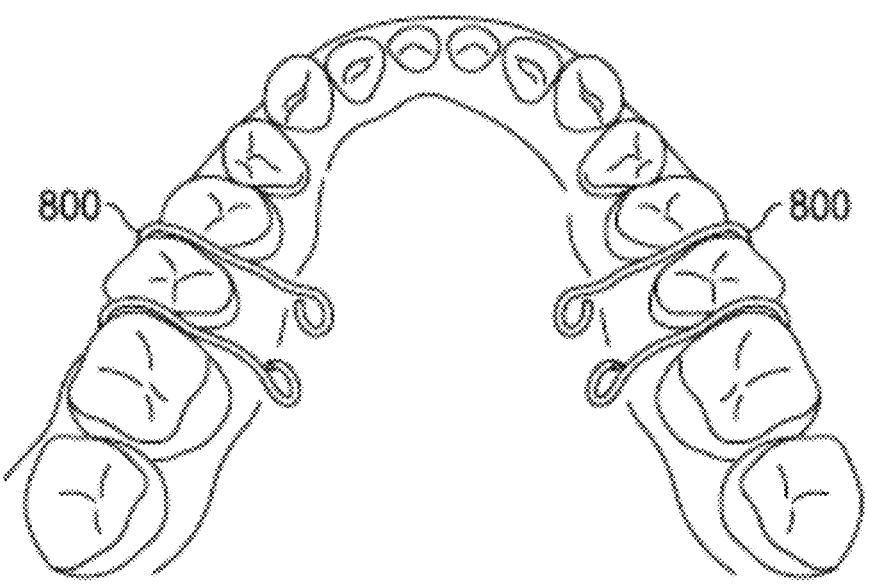
FIG. 8A is a U-shaped spring, in this case fitted on the ends with balls, as is typically used in orthodontic devices.
Figure 8B:
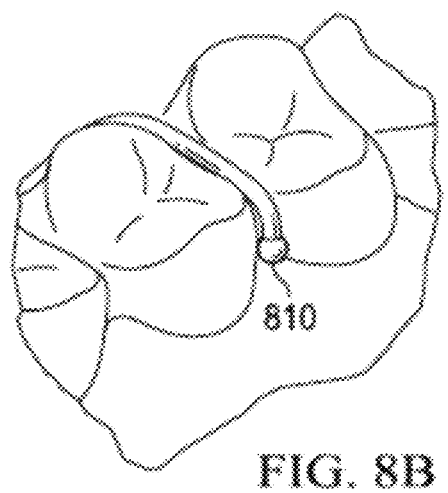
FIG. 8B shows a similar device, where one end is a hook, and the other ends in a small eye (optional).
Figure 8C:
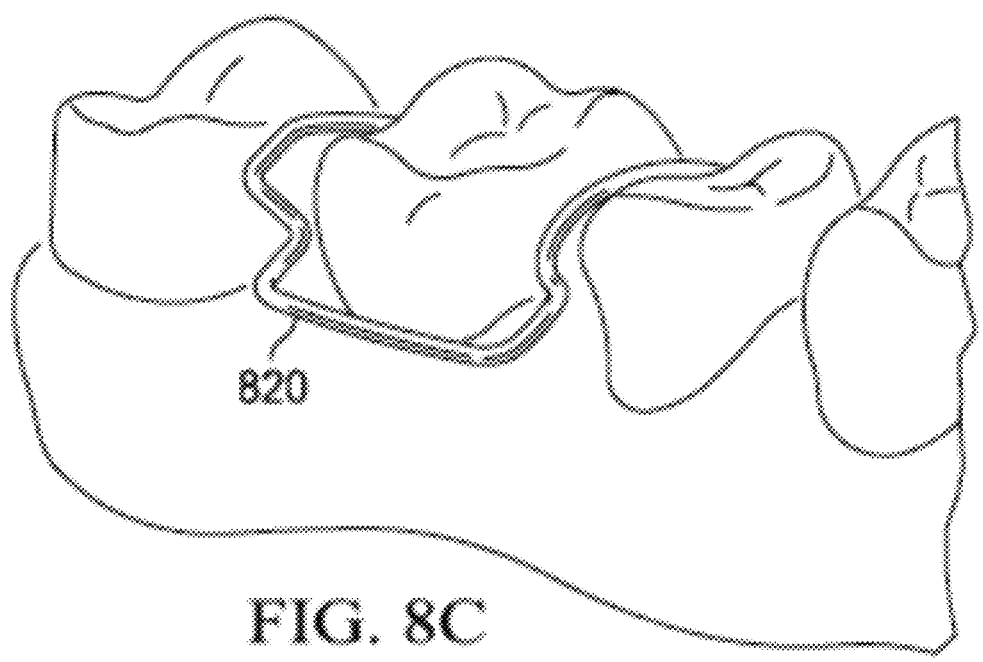
FIG. 8C shows a larger spring clasp that connects over 2 or 3 teeth. In these figures, the strip is omitted for clarity, but the same clips can hold a strip or plate against an aligner.

Each of the embodiments of FIGS. 6 and 7 require modification to the aligner be provided so that an attachment means can connect thereto, and therefore, these embodiments may be less preferred. It is however, possible to provide a mechanical clip for attaching a strip or plate to the aligners for the approximately twenty minutes of daily usage that avoids the need for a dedicated attachment point on the aligner. FIG. 8A-C show three variant clips in position as clipped over teeth. The vibrating strip and/or plate is not shown herein for clarity, but clips such as 800, 810, 820 could easily be used to hold a vibrating strip or plate in position against an aligner for temporary use. In such embodiments, no adhesive, magnetic elements or other attachment means need be provided for either the vibrating strip or the aligner. As such, providing spring clips such as those shown may be a preferred embodiment.

Figure 9:
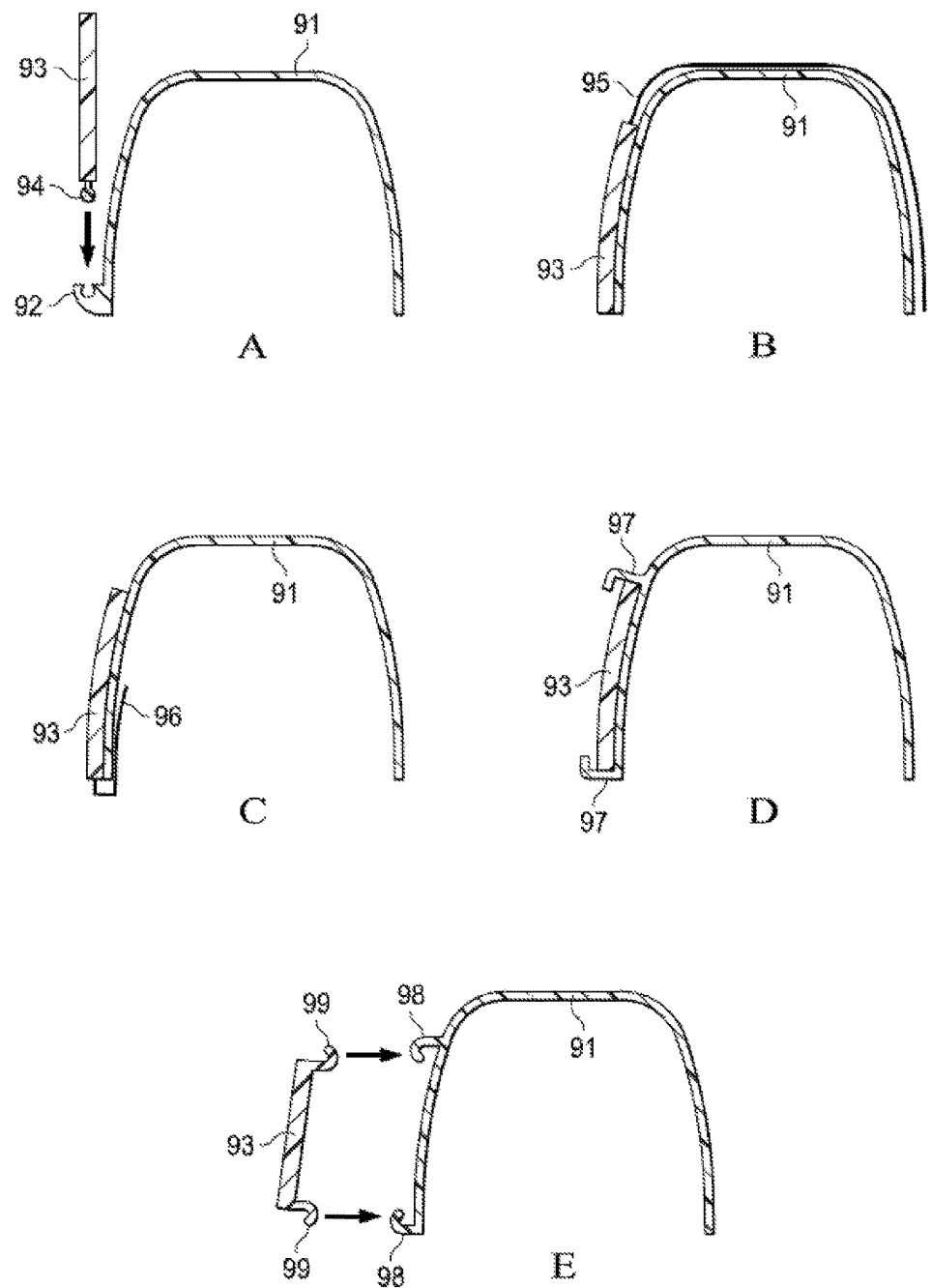
FIG. 9 shows various strip and retainer attachment means in cross section.

FIG. 9 illustrates a variety of snap fit or hook type attachment means used with a vibrating strip, shown in cross section. FIG. 9A shows a snap fit 94 fitting into the corresponding socket 92 on the aligner 91, thus allowing the vibrating strip 93 to snap into place alongside the aligner 91. While a ball and socket are shown, any suitable snap fit, including cantilevered snap fits, can be used. The orientation of the snap fit can also be changed. Here shown, the snap fit is in the same axis as the vertical axis of the vibrating strip, but attachment means can also be perpendicular thereto, as shown in FIG. 9E, and such may be preferred as providing a more stable attachment.

FIG. 9B shows a strip 93 with hook 95 that fits over aligner 91. A pair of hooks at each end, and possibly a central hook for a long strip, will serve to hold the vibrating strip in place during use. FIG. 9C shows a similar strip 93 and hook 96 design, but in this case the hook fits under the aligner 91.

FIG. 9D shows a retainer 91 fitted with a bracket 97, into which slides a strip 93. The bracket can run the length of the aligner, or can be comprised on a plurality of shorter brackets. As with all aligner modifications, the attachment means can be added thereto, but is preferably integral and made as part of the 3D scanning and modeling process. Another variation is shown in FIG. 9E where the aligner 91 has hooks 98 which couple with hooks 99 on the strip 93. Attachment means are shown throughout as larger than actually needed for clarity of the graphics.

Once attached, the patient can activate the on/off switch of the strip or plate with the tongue or fingertip, and vibrate for the desired time period, e.g., every few days, daily, or more frequently. Alternatively, if small enough, the device can be left in place for the week duration of use, and the device can be programmed to self-activate 1×, 2×4× during the day.

In use, the protective strip (usually paper, teflon, waxed paper, nonstick plastic, and the like), is removed, and the vibrating strip applied to a aligner 10 or positioner or fixed device or even applied directly to the teeth (e.g., with braces on the facial surfaces, the strip can be applied to the lingual surfaces. We anticipate that this strip can be made inexpensively enough that the patient can purchase a dozen or two, to be used with the various aligners made throughout the course of his or her treatment. The other embodiments are used in a similar way, being attached to the aligner by whatever attachment means was provided, and the vibrating device is activated for e.g., 20 minutes a day.

While the invention is described above in detail, it should be understood that various changes, substitutions, and alterations could be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

Each of the following is incorporated by reference in its entirety.

60/906,807 (Mar. 14, 2007), US2008227046, US2008227047, US2010055634, US20120040300, US2013059263, US20130322018, WO2010093632, PCT/US13/36289, 61/624,242 (Apr. 13, 2012), PCT/US13/36289 (Apr. 13, 2013), 61/615,480 (Mar. 26, 2012), Ser. No. 13/850,151 (Mar. 25, 2013), 61/824,798 (Jul. 19, 2013), 61/769,507 (Sep. 13, 2012) and 61/673,236 (Jul. 18, 2012), Ser. No. 13/934,651 (Jul. 16, 2013) and all applications and patents related thereto.

Chung How Kau, et al., The clinical evaluation of a novel cyclical force generating device [AcceleDent®] in orthodontics, Orthodontic Practice 1(1): 10-15 (2010).

Kopher R A and Mao J J. Suture growth modulated by the oscillatory component of micromechanical strain. 2003. J. Bone and Min Res. 18 (3). pp. 521-528.

Nishimura et. al. Periodontal tissue activation by vibration: Intermittent stimulation by resonance vibration accelerates experimental tooth movement in rats. 2008. Am J Orthod Dentofacial Orthop 133(4) pp. 572-583.

Peptan A I, et. al. Responses of intramembranous bone and sutures upon in-vivo cyclic tensile and compressive loading. 2008. Bone (42) pp. 432-438.

Vij K. and Mao, J J. Geometry and cell density of rat craniofacial sutures during early postnatal development and upon in-vivo cyclic loading. 2006. Bone (38) pp. 722-730.

Krishtab et al., [Use of vibratory action on the teeth to accelerate orthodontic treatment] [Article in Russian] Stomatologiia (Mosk). 1986 May-June; 65(3):61-3.

The invention claimed is:

1. A flat planar vibrating orthodontic remodeling device for use with a separate orthodontic remodeling appliance, comprising:
   a) a flat planar strip having a flat back surface and a flat front surface;
   b) said flat planar strip having one or more vibratory sources thereon operably connected to one or more power sources;
   c) said flat back surface being peel-and-stick and having an adhesive layer for reversibly coupling to said separate orthodontic remodeling appliance and a removable protective coating over said adhesive layer; and,
   d) wherein said orthodontic remodeling device is hermetically sealed and can vibrate at a frequency of 1-40 Hz and a force of 0.1-0.5 Newtons.

2. The orthodontic remodeling device of claim 1, wherein said front surface is smoothly rounded at a top edge and a bottom edge, and flat between said edges.

3. The orthodontic remodeling device of claim 1, wherein said power source is a coin battery.

4. The orthodontic remodeling device of claim 1, wherein said power source is a charged capacitor.

5. The orthodontic remodeling device of claim 1, wherein said vibratory source is a coin vibrator.

6. The orthodontic remodeling device of claim 1, further comprising an on/off switch.

7. The orthodontic remodeling device of claim 1, further comprising a processor programmed to automatically activate said device at least twice per day for a period of at least one minute.

8. The orthodontic remodeling device of claim 1, further comprising a waterproof silicone coating.

9. The orthodontic remodeling device of claim 1, wherein said power source is a coin battery, said vibratory source is a coin DC motor vibrator, and wherein said planar strip has a waterproof silicone coating.

10. The orthodontic remodeling device of claim 1, said device being able to vibrate at 30 Hz at a force of 0.2-0.25 Newtons.

11. The orthodontic remodeling device of claim 1, said vibrator being able to vibrate at 5-30 Hz and 0.1-0.3 Newtons.

12. The orthodontic remodeling device of claim 1, said device having a noise level less than 55 dB when measured at 6 inches, and being capable of vibrating at a frequency between 20-40 Hz with a variance of only 2 Hz, and a force between 0.1-0.5 Newtons with a variance of +−0.05 N.

13. The orthodontic remodeling device of claim 1, further comprising a processor for controlling said vibratory source.

14. The orthodontic remodeling device of claim 13, wherein said vibratory source is a piezoelectric motor.

15. An orthodontic remodeling system, comprising:
   a) an aligner shaped to closely fit teeth and apply an orthodontic remodeling force to one or more teeth;
   b) a vibrating flat strip or plate shaped to fit against a lingual or occlusal surface of said aligner, said vibrating flat strip or plate being hermetically sealed and vibrating at a frequency between 1-40 Hz and a force between 0.1-0.5 Newtons when in use; and,
   c) peel-and-stick attachment means for reversibly coupling said aligner to said vibrating flat strip or plate.

16. The orthodontic remodeling system of claim 15, wherein said attachment means is selected from an adhesive, a magnet and magnetically responsive metal insert, a snap fit connector and socket, one or more hooks, or a spring clip.

17. A method of orthodontic remodeling, comprising wearing the aligner of claim 15 about 22-24 hours a day, applying said vibrating flat planar strip or plate to said aligner using said attachment means, and activating said vibrating device for about 20 minutes a day.

18. A method of orthodontic remodeling, comprising wearing an orthodontic remodeling device, applying a peel-and-stick, flat planar, waterproof, vibrating strip that vibrates at a frequency between 20-40 Hz and a force between 0.1-0.3 Newtons to said orthodontic remodeling device, and activating said vibrating strip for a period of time.

19. A faster method of orthodontic remodeling, comprising a patient wearing an aligner about 22-24 hours daily, said patient applying a peel-and-stick vibrating device to said aligner, said vibrating device shaped to fit against a lingual or occlusal surface of said aligner, and activating said vibrating device for about 20 minutes a day, wherein the time needed for orthodontic remodeling is about half that needed when said aligner is used alone without said vibrating device.

* * * * *